United States Patent
Dasari et al.

(12)

(10) Patent No.: US 9,315,764 B1
(45) Date of Patent: Apr. 19, 2016

(54) METHOD OF PROCESSING PHOSPHOLIPID BASED LIPID MATERIALS

(75) Inventors: Mohan Prasad A. Dasari, West Des Moines, IA (US); Abdullah A. Mahfuz, Johnston, IA (US)

(73) Assignee: RRIP, LLC, Pleasant Hill, IA (US)

( * ) Notice: Subject to any disclaimer, the term of this patent is extended or adjusted under 35 U.S.C. 154(b) by 876 days.

(21) Appl. No.: 12/771,725

(22) Filed: Apr. 30, 2010

Related U.S. Application Data

(60) Provisional application No. 61/174,731, filed on May 1, 2009.

(51) Int. Cl.
*C12P 7/64* (2006.01)
*C11B 13/02* (2006.01)
*C11B 1/02* (2006.01)

(52) U.S. Cl.
CPC . *C11B 13/02* (2013.01); *C12P 7/64* (2013.01); *C11B 1/025* (2013.01)

(58) Field of Classification Search
None
See application file for complete search history.

(56) References Cited

U.S. PATENT DOCUMENTS

| | | | | |
|---|---|---|---|---|
| 6,399,802 | B2 * | 6/2002 | Reaney | 554/179 |
| 6,423,857 | B1 * | 7/2002 | Copeland et al. | 554/198 |
| 6,475,758 | B2 * | 11/2002 | Reaney | 435/134 |
| 6,844,458 | B2 * | 1/2005 | Copeland et al. | 554/212 |
| 7,494,676 | B2 * | 2/2009 | Chakrabarti et al. | 426/33 |
| 7,598,407 | B2 * | 10/2009 | Kruidenberg | 554/22 |
| 7,977,080 | B2 * | 7/2011 | Gramatikova et al. | 435/198 |
| 2009/0173689 | A1 * | 7/2009 | Dayton | 210/632 |

OTHER PUBLICATIONS

Haas et al., JAOCS, 72(5):519-525, 1995.*

* cited by examiner

*Primary Examiner* — Jennifer McDonald
*Assistant Examiner* — Qing Xu
(74) *Attorney, Agent, or Firm* — Brick Gentry PC; Brian J. Laurenzo; Jessica L. Susie

(57) ABSTRACT

The present invention provides methods of processing lipid materials such as soapstock, wet gums and dry gums. Enzymes are utilized to catalyze hydrolysis of the lipids materials to recover fatty acids. Addition of organic acids and/or polyols improved yield of fatty acids and reduced formation of emulsion. Lipid materials can be formulated with other agricultural products as new value-added animal fee products.

13 Claims, No Drawings

METHOD OF PROCESSING PHOSPHOLIPID BASED LIPID MATERIALS

CROSS-REFERENCE TO RELATED APPLICATIONS

This application claims the benefit of U.S. Provisional Patent Application Ser. No. 61/174,731, filed May 1, 2009, and entitled "Enzymatic Processing of Lipid Materials", which is incorporated herein by reference.

BACKGROUND OF THE INVENTION

1. Field of the Invention

This invention relates to the field of chemical processing, and more particularly to processing crude vegetable oil.

2. Description of the Related Art

Crude vegetable oils predominantly contain triglycerides along with some impurities such as free fatty acids, phospholipids, etc. These impurities are typically removed from crude oil by vegetable oil refining process. The first step in the refining process is degumming where the oil is treated with aqueous acid solution to remove both hydratable and non-hydratable phospholipids. These phospholipids are separated from the oil by centrifugation and are commonly known as wet gums. Wet-gum is a dark brown to blackish in color, highly viscous product comprising of phosphatides, water, triglycerides, and free fatty acids. The degummed oil is then treated with aqueous alkali (typically sodium or potassium hydroxide) in order to remove the free fatty acids. The alkali reacts with the free fatty acids present in the crude glycerides to form soap. The soap and other solid impurities are separated from the refined oil by centrifuging and are generally known as "soapstock" or "foots". The soapstock obtained from this process is known as degummed soapstock and typically contains vegetable oil, water, soap, and traces of phospholipids. Alternately, in some current oil refineries the phospholipids and soapstock is removed simultaneously. The soapstock from this alternate process is known as gummed soapstock and typically contain vegetable oil, phospholipids, water and soap. Soapstock is alkaline in nature due to the presence of unreacted alkali. The refined oil is further processed.

Both wet gums and soapstock have commercial value as a source of fatty acids. Fatty acids can be recovered from wet gums and soapstock by hydrolysis. Wet gums are currently being sold as a raw material for lecithin production and for animal feed blending. Wet-gum contains phospholipids mostly phosphatidylcholine which is necessary for mobilization of fat out of the liver and also improves breeding performance and milk production of an animal. The wet gums can be dried using an evaporator to a low moisture product known as dry gums. The wet gums and dry gums products although nutritionally desirable and abundantly available in the market find limited application in feed due to their handling and storage difficulties.

Fatty acids can be recovered from soapstock as a valuable product. A product high in fatty acid content (generally about 55-65% free fatty acids) is obtained from the soapstock by acidulation with a mineral acid such as sulfuric or hydrochloric acid. The conventional way of acidulating soapstock is to react it with acid solution at an elevated temperature under continuous agitation. The gummed soapstock typically contains considerable amounts of phospholipids (gums) which act as emulsifiers, for which reason a very long settling time may also be necessary to get acid oil of acceptable purity. If the acidulated soapstock is allowed to settle, it separates into three layers. The bottom layer is an acidic aqueous solution which can be pumped off and recycled. The top layer is the desired fatty acid product, known as acid oil, which may be used as is (e.g., for animal feed), or may be further treated to obtain more highly purified fatty acids (e.g., by distillation). The middle layer is an emulsified sludge material, a semi-solid, emulsified layer containing primarily phospholipids, water, and a substantial quantity of the desired fatty acid product entrained therein. With the soapstock containing large amounts of gums and impurities it is often difficult to obtain a complete separation of the phases and may give rise to considerable amount of emulsion layer resulting in significant loss of the acid oil. Also, due to the corrosive nature of the sulfuric acid and the acidulated water the necessary protection against the corrosion make relatively simple equipment rather expensive and the maintenance costs are often considerable.

As a consequence of the foregoing situation, there has existed a longstanding need for a new and improved method of processing crude vegetable oils and the provision of such a method is a stated objective of the present invention.

BRIEF SUMMARY OF THE INVENTION

Briefly stated, the present invention provides a method utilizing enzymes to catalyze the soapstock acidulation process, and methods of processing wet and dry gums as feed stock to produce acid oil, and to formulate new value-added animal feed products.

An objective of this invention is to utilize enzymes such as protease, lipase, phospholipase, etc., to catalyze the soapstock acidulation reaction.

Both wet gums and dry gums have high fatty acid content, as compared to soapstock, and can be used as an alternate feedstock for producing fatty acids in high yields. Another method of invention is to research and develop novel methods to process both wet and dry gums as new source of feed stock to produce acid oil or to develop new value-added products.

DETAILED DESCRIPTION OF THE INVENTION

This invention describes the use of enzymes to catalyze the soapstock acidulation process, methods of processing food stock of wet and dry gums to produce acid oil, and animal feed formulations utilizing wet and dry gums.

Overall objective of this study is to research and develop alternate methods to treat the vegetable oil refining by products i.e., soapstock, wet gums, dry gums. One of the methods of invention is to utilize enzymes such as protease, lipase, phospholipase, etc., to catalyze the soapstock acidulation reaction. Following are the advantages of the enzymatic processing of current invention over the conventional acidulation process.

1. The enzymes are used to convert the soap into free fatty acids and are further used to hydrolyze the gums (phospholipids) into free fatty acids and corresponding phosphatide molecules. This results in little or no formation of middle emulsion layer, after settling thereby eliminating the loss of acid oil through the emulsion layer.

2. The enzymes are usually very active at a neutral pH range and hence the reaction is conducted at a pH range of about 6-7 as compared to the usual acidulation pH of 1.5-2. This reduces the usage of sulfuric acid and makes this a very environmentally friendly, green process.

3. In the conventional process there is a high chance for degradation of neutral oil and other lipid components as a result of oxidation at the acidic process conditions. In the enzymatic process, the acid oil produced will have a higher quality viz. (a) higher neutral oil content (b) lighter golden-brown color (c) higher oxidative stability (d) higher amount of nutraceuticals such as sterols, tocopheorls, etc.

4. The acid water generated in conventional process has a pH in the range of 1-1.5 and it has to be further neutralized with caustic for safer handling and disposal. The resultant water from the enzymatic process will be at a neutral pH range and hence does not have to be neutralized.

5. In the enzymatic process, a centrifuge system can be used to separate the individual components of acidulated soapstock. This option if fairly limited in the conventional process due to the low process pH. Utilizing a centrifuge for separation, instead of gravitational settling, will tremendously reduce the process time, and also help extract most of the oil from the emulsion phase.

| Conventional Process | Enzymatic Process |
|---|---|
| 1. Low pH process- typically 1.5 to 2 pH | Higher pH-typically in the neutral pH range |
| 2. Primarily hydrolyzes soap | Hydrolyzes soap as well as phospholipids |
| 3. More emulsion layer | Little or no emulsion layers |
| 4. Oil yield loss through emulsion layer | Reduced oil loss |
| 5. Corrosive process | Green process |
| 6. Low neutral oil in the final product | Higher neutral oil |
| 7. Dark brown-black color of oil | Lighter golden-brown color |
| 8. Oil is susceptible for oxidation | Higher oxidative stability |
| 9. High degradation sterols and tocopherols | Less degradation of sterols and tocopherols |
| 10. Acid water needs neutralization for disposal | No treatment of water is necessary |
| 11. Centrifuge cannot be used for separation-low pH | Centrifuge can be used for separation |

Materials and Methods

The soapstocks used in this study are obtained by alkali refining of degummed or gummed vegetable oil from three different vegetable oil refineries.

| Soapstock | TFA Range (%) | Moisture Range (%) | Phospholipids Range (5) | pH Range (%) |
|---|---|---|---|---|
| Soapstock A | 15-40 | 45-70 | 5-10 | 8-10 |
| Soapstock B | 15-40 | 40-70 | 5-10 | 8-10 |
| Soapstock C | 15-55 | 30-75 | 0-2 | 6-8 |

Moisture of the soapstock was adjusted to 70% for better mixing

A 40 g sample of soapstock was heated to 80° C., stirred at approximately 100 rpm while concentrated sulfuric acid was slowly added. Ten minutes of blending time is allowed between each acid addition and pH measurement. Upon reaching a desired of pH (<2), the moisture was allowed to settle in an 80° C. oven for eight hours. After settling, the oil, water and emulsion fractions/layers were measured and then the sample is centrifuged at 3000 RCF for three minutes to record the changes between separation techniques.

A 40 g same of soapstock was heated at 55° C. and started stirring at approximately 100 rpm. As needed, pH of the soapstock is adjusted to the working pH of the enzyme. Upon reaching a desired pH, enzyme was added at 2% concentration of the soapstock (db). The reaction mixture was incubated for two hours and then settled in an 80° C. over for eight hours. After settling, the individual fractions/layers were measured and then the sample was centrifuged at 3000 RCF for three minutes to record the changes between separation techniques. A blank experiment (as –ve control) was run without using an enzyme. Table 1A shows the list of enzymes and their average working pH.

TABLE 1A

List of enzymes, their types and average working pH used in this study.

| Enzyme type | Optimal pH range | Average working pH |
|---|---|---|
| Phospholipase A1 | 5.0-5.5 | 5.0 |
| Phospholipase A2 | 5.0-8.0 | 7.0 |
| Phospholipase C | 6.0-7.5 | 7.0 |
| Lipase | 5.0-5.5 | 5.0 |
| Protease | 7.0-10 | 7.0 |

Calculations:

% Oil = volume of oil/total volume × 100

% Emulsion = volume of Emulsion/total volume × 100

% Water = volume of Water/total volume × 100

Results
Soapstock A (53% moisture, 32% TFA and 6.3% phospholipids)

| Treatment | | | Settling for 8 hours | | | Centrifugation | | |
|---|---|---|---|---|---|---|---|---|
| No | Enzyme | pH | Oil % | Emulsion % | Water % | Oil % | Emulsion % | Water % |
| 1 | +ve control | 1.25 | 32 | 16 | 52 | 36 | 7 | 57 |
| 2 | –ve control | 5.74 | | no separation | | 23 | 77 | none |
| 3 | Phospholipase A1 | 5.74 | 32 | 2 | 67 | 32 | 2 | 66 |
| 4 | Phospholipase A2 | 6.30 | 33 | 13 | 54 | 36 | 0.6 | 64 |
| 5 | Phospholipase C | 6.17 | 9 | 21 | 70 | 17 | 3 | 80 |
| 6 | Lipase | 5.2 | 21 | 11 | 68 | 24 | 7 | 68 |
| 7 | Protease | 6.17 | Oil & Emulsion mixed | | 67 | 14 | 19 | 67 |

Based on above table, it can be stated that phospholipase A2 and phospholipase A1 will work on soapstock A splitting. Enzymatic treatment improved oil yield and decreased the emulsion layer. It was also observed that the color of the oil and water is lighter than the positive control. It was also observed that centrifugation of the reaction mixture resulted in a better oil yield.

In this study, the treatment conditions were controlled in order to compare between an untreated and treated sample. Therefore, the treatment condition should not be considered as optimal condition for the above listed enzymes.

| Soapstock B (53% moisture, 25% TFA and 0.3% phospholipids) | | | | | | | |
|---|---|---|---|---|---|---|---|
| | Treatment | Settling for 8 hours | | | Centrifugation | | |
| No Enzyme | pH | Oil % | Emulsion % | Water % | Oil % | Emulsion % | Water % |
| 1 +ve control | 1.70 | 24 | 6 | 70 | 28 | 2 | 70 |
| 2 −ve control | 6.74 | Oil & Emulsion mixed | | 62 | Oil & Emulsion mixed | | 62 |
| 3 Phospholipase A1 | 5.12 | Oil & Emulsion mixed | | 67 | 29 | 4 | 67 |
| 4 Phospholipase A2 | 6.74 | Oil & Emulsion mixed | | 66 | 31 | 4 | 66 |
| 5 Phospholipase C | 6.74 | Oil & Emulsion mixed | | 54 | 31 | 4 | 65 |
| 6 Lipase | 6.05 | Oil & Emulsion mixed | | | Oil & Emulsion mixed | | |
| 7 Protease | 6.74 | 31 | 13 | 56 | 32 | 1 | 67 |

A variety of enzymes including protease seemed to work on soapstock B. Enzymatic treatment yielded more oil than the positive control. The viscosity of the oil from enzymatic treatment is lower than negative control but higher than the positive control. The higher viscosity is due to suspended water and gums in the oil phase. At higher pH, water and gums may get trapped in the oil phase making it difficult to separate. The reaction conditions may have to be optimized in order to facilitate better separation of the layers.

lose moisture and begin to coagulate. Addition of water to the wet did not reduce the viscosity to a great extent. Therefore, an ideal solvent will reduce the viscosity of the wet gums, does not interfere in the reaction (stable), less volatile, cheap and has low solubility in the oil phase. Glycerin was considered as a solvent because it satisfies our requirements and it is also available in abundance as a by-product of biodiesel industry.

| Soapstock C (52.9% moisture, 29.2% TFA and 5.4% phospholipids) | | | | | | | |
|---|---|---|---|---|---|---|---|
| | Treatment | Settling for 8 hours | | | Centrifugation | | |
| No Enzyme | pH | Oil % | Emulsion % | Water % | Oil % | Emulsion % | Water % |
| 1 +ve control | 1.14 | Very little oil separation | | | 23 | 19 | 58 |
| 2 −ve control | 6.91 | 14 | 38 | 48 | 21 | 23 | 56 |
| 3 Phospholipase A1 | 5.09 | 29 | 14 | 57 | 25 | 8 | 67 |
| 4 Phospholipase A2 | 6.91 | 18 | 21 | 61 | 24 | 12 | 64 |
| 5 Phospholipase C | 6.91 | Oil & Emulsion mixed | | | Oil & Emulsion mixed | | |
| 6 Lipase | 5.09 | 29 | 6 | 65 | 28 | 5 | 67 |
| 7 Protease | 6.91 | Oil & Emulsion mixed | | | Oil & Emulsion Mixed | | |

Based on enzymatic treatment on soapstock C, it was observed that lipase, phospholipase A1 and phospholipase A2 worked better.

Materials and Methods:

Wet-gum and dry gum samples were obtained from two different vegetable oil refineries. Typical composition of all of gum materials used in this study are shown in Table 1. The wet gum sample was kept in refrigerator until used and were thawed for about 30 minutes, mixed thoroughly and then samples were collected for analysis and experiments.

TABLE 1

Analysis of various gum samples

| Component | Wet gums | Dry gums |
|---|---|---|
| Oil (%) | 10-25 | 25-35 |
| Free Fatty Acids (%) | 0.5-5 | 10-15 |
| Acetone Insolubles (%) | 40-55 | 50-60 |
| Phospholipids (%) | 30-55 | 40-50 |
| Moisture (%) | 25-40 | 1-5 |
| Total Fatty Acids (%) | 35-50 | 60-70 |

Wet gums and dry gums are highly viscous and create a major issue during the treatment/processing. The viscosity of the gum slight reduces with increase in the temperature. However, as the temperature is increased further, the gum starts to

TABLE 2

Effect of glycerin addition on viscosity of wet gums

| Amount of 50% glycerin | Viscosity Range, SSU |
|---|---|
| 40% | 3,000-5,000 |
| 20% | 15,000-20,000 |
| 10% | 15,000-20,000 |
| 5% | 30,000-40,000 |
| 0% | 40,000-50,000 |

Based on above study, it was observed that addition of glycerin reduced the viscosity of wet gums and increased the flowability and mixing capability at 80° C. temperature. It was also observed that 50% diluted glycerin performed more effectively than concentrated glycerin. Glycerin was also able to reduce the viscosity of dry gums as well.

Results and Discussion:

Several options were evaluated to process the gum type materials. Out of the available options, on basis of their feasibility, four options were chosen to be studied further.

A. Option 1: Enzymatic Hydrolysis of gums

B. Option 2: Chemical Hydrolysis of gums

C. Option 3: Liquid feed/mold inhibitor product by combining with organic acids

D. Option 4: Dry feed product by combining with agricultural co-products

Each option is described separately in the following pages

A. Option 1: Enzymatic Hydrolysis of Gums

Wet gum was treated with enzymes such as Phospholipase A1, Phospholipase A2, and Phospholipase C for 20 hours at 50° C. and pH at around 6. Higher amount of enzyme was used in order to evaluate the efficacy of the enzyme for the hydrolysis reaction. Once the enzymes are identified, the conditions can be further optimized in order to make it feasible for the commercial scale production. Among these enzymes, Phospholipase A2 and Phospholipase C were more effective. They released more clear oil with some amount of middle emulsion phase still existing. Other enzymes showed same result as a negative control (data not shown). Subsequently, some other experiments were carried out using Phospholipase A2 enzyme and other combinations like glycerin, acid oil as solvent. pH of the wet gums was adjusted to desired pH with NaOH. The reaction was carried out at 45-50° C. with constant stirring. After 20 hours reaction the sample was heated to 90° C.-95° C. in an oven for 10 minutes to inactivate the enzyme and then transferred to a centrifuge tube followed by centrifugation at 3000 rpm for three minutes.

TABLE 3

Results of enzymatic hydrolysis of wet gums

| No | Treatment | Treatment pH | Oil yield, g | Oil yield, % |
|---|---|---|---|---|
| 1 | 100 g Wet gums (Control) | 5.8 | 0 | 0 |
| 2 | 100 g Wet gums + 0.25% Phospholipase A2 | 7 | 17 | 43 |
| 3 | 100 g Wet gums + 2% Phospholipase A2 | 5.8 | 30 | 75 |
| 4 | 100 g Wet gums + 20 g glycerin (Control) | 5.3 | 0 | 0 |
| 5 | 100 g Wet gums + 20 g glycerin + 0.5% Phospholipase A2 | 5.4 | 29 | 73 |
| 6 | 100 g Wet gums + 16 g water + 0.5% Phospholipase A2 | 5.2 | 20 | 50 |

Based on the results in Table 3, it can be concluded that, due to high viscosity of the gums, enzyme Phospholipase A2 alone may be able to hydrolyze the wet gums. Addition of water, fusel oil, isopropanol and propylene glycol (data not shown) to wet gums showed a slight increase on the oil but no water was separated. On the other hand, when wet gum was mixed with acid oil and glycerin the viscosity was reduced facilitating the enzymatic reaction.

Dry gum pH was adjusted using 4M NaOH. The reaction was carried out at 45° C. for Phospholipase A2 and 60° C. for Phospholipase C with constant stirring for 20 hrs. Once incubation was done the emulsion was put in a 90° C. oven for 10 min to inactivate the enzyme and then centrifuged at 3000 rpm for three minutes. Table 4 shows the result of enzymatic treatment of dry gums. Phospholipase A2 yielded more oil than Phospholipase C at same enzyme concentration. A clear oil phase with a bottom emulsion layer was observed in all the cases.

TABLE 4

Enzymatic Hydrolysis of Dry Gums

| No | Treatment | Treatment pH | Oil yield, g | Oil yield, % |
|---|---|---|---|---|
| 1 | 100 g Dry gums (Control) | 5.9 | 6 | 10 |
| 2 | 100 g Dry gums + 0.5% Phospholipase A2 | 5.7 | 18 | 28 |
| 3 | 100 g Dry gums + 2% Phospholipase A2 | 5.9 | 51 | 81 |
| 4 | 100 g Dry gums + 20 g glycerin + 1% Phospholipase A2 | 5.3 | 19 | 30 |
| 5 | 100 g Dry gums + 20 g glycerin + 10 g water + 0.5% Phospholipase A2 | 5 | 33 | 52 |
| 6 | 100 g Dry gums + 100 g wet gums + 20 g glycerin 0.25% Phospholipase A2 | 5.9 | 33 | 63 |
| 7 | 100 g Dry gums + 2% Phospholipase C | 6.7 | 34 | 54 |

B. Option 2: Chemical Hydrolysis of Gums

About 80 g of sample was heated to 80° C., mixed with a solvent as needed and stirred at approximately 100 rpm while concentrated sulfuric acid was slowly added. Ten minutes of blending time is allowed between each acid addition and pH measurements. Upon reaching a desired pH (<2), the mixture was settled in an 80° C. oven for eight hours.

Wet gum was mixed with various solvents and then hydrolyzed (Table 5). Among these solvents propionic acid gave the highest oil yield. The viscosity of wet gums significantly reduces when it is mixed with propionic acid. This indicated that most phospholipids are soluble in propionic acid facilitating the hydrolysis reaction. Addition of propionic acid as solvent, therefore, increased the oil yield and significantly reduced the emulsion yield. However, the addition of propionic acid significantly increased the moisture content of the oil as compared to the control. Propionic acid concentration from 10% and 5% resulted in 14.4% to 3.61% moisture content in the oil, respectively. Addition of 10% acetic acid as a solvent resulted in similar oil yield as well as lower moisture (4.6%) content in the oil phase. This indicates that the propionic acid, due to its intermediate polarity, has a tendency to act as a co-solvent for oil, water and phospholipids thereby dissolving some moisture and phospholipids in the oil phase. On the other hand, acetic acid with a higher polarity, as compared to acetic acid, does not have a tendency to co-dissolve water and phospholipids in the oil phase. Higher amount of organic acid may facilitate better reaction of wet gums but will result in higher moisture content in the oil phase. Therefore, based upon the phospholipid content, the amount of organic acid has to be optimized in order to get a higher oil yield with low moisture content in the oil phase. It was hypothesized that combination of organic acid and other favorable solvent might increase oil yield as well as reduce moisture in the oil phase. In order to verify the hypothesis diluted propionic acid, glycerin, phosphoric acid, propylene glycol, methanol, vinegar, oleic acid, acid oil and fusel oil were used as solvents. Out of all the solvent glycerin had oil yield that is comparable to addition of organic acid. As shown before addition of glycerin decreased emulsion viscosity and increased flowability, therefore glycerin was used as a solvent in combination with propionic acid for further study. As shown in Table 5, the combination of glycerin and propionic/acetic acid although slightly reduced the oil yield produced high quality oil low moisture. Glycerin helps in not only reducing the viscosity of the gums but, due to its high polarity, also reduces the moisture and phospholids from the oil phase. Hydrochloric acid performed similar to sulfuric acid during hydrolysis.

TABLE 5

Chemical hydrolysis of wet gums

|   |   |   | 8 hour settling | | | Moisture in oil |
| --- | --- | --- | --- | --- | --- | --- |
| No | Treatment | End pH | Oil % | Emulsion % | Water % | phase, % |
| 1 | Wet gums control | 4.0 | No separation occurred | | | |
| 2 | Wet gums + Sulfuric acid (SA) | 1.43 | 42 | 58 (Emulsion & water coagulated) | | 0.23 |
| 3 | Wet gums + 10% Propionic Acid (PA) + SA | 2.58 | 58 | 9 | 33 | 14.4 |
| 4 | Wet gums + 5% PA + SA | 1.89 | 48 | 16 | 36 | 3.61 |
| 5 | Wet gums + 10% Acetic Acid (AA) + SA | 1.70 | 65 | 6 | 29 | 4.60 |
| 6 | Wet gums + 10% PA + Hydrochloric acid (HCl) | 1.8 | 54 | 3 | 43 | 7.54 |
| 7 | Wet gums + 10% AA + HCl | 1.72 | 49 | 11 | 41 | 1.79 |
| 8 | Wet gums + 20% Glycerin (GLY) + SA | 1.9 | 36 | 42 | 22 | |
| 9 | Wet gums + 10% GLY + 5% PA + SA | 1.84 | 44 | 22 | 34 | 1.49 |

Mass Balance Study for Chemical Hydrolysis of Wet Gums

Based on the above results mass balance study is performed on three different treatments of wet gums. In 400 g wet gum, calculated amount of propionic acid and 50% glycerin solution was added. The contents were mixed thoroughly and hydrolyzed with sulfuric acid to pH of 1.5-2. Table 6 shows the mass balance of different treatments.

TABLE 6

Mass balance of wet gums hydrolysis with different solvent treatments

| Fraction | Fraction wt. (g) | Moisture (%) | TFA (%) | TFA (g) | TFA Yield (%) |
| --- | --- | --- | --- | --- | --- |
| a) Hydrolysis using 10% propionic acid and sulfuric acid | | | | | |
| Oil | 220 | 14.4 | 79.6 | 175 | 99.4 |
| Emulsion | 20 | 37.2 | | | |
| Water | 180 | 58.7 | | | |
| b) Hydrolysis using 5% propionic acid, 10% gycerin and sulfuric acid | | | | | |
| Oil | 170 | 5.8 | 90.1 | 153.2 | 87 |
| Emulsion | 70 | 24.3 | | | |
| Water | 230 | 57.8 | | | |
| c) Hydrolysis using with 20% glycerin and sulfuric acid | | | | | |
| Oil | 130 | 1.2 | 98.4 | 127.9 | 72.7 |
| Emulsion | 150 | | | | |
| Water | 210 | 42.2 | | | |

Note:
Treatments (a) and (b) may contain some residual propionic acid entrained in the oil phase. Weight of wet gums = 400 g, Theoretical TFA = 176 g Two Stage Chemical Hydrolysis of Wet Gums:

As an alternate processing method, wet gums were processed in two stages. In the first stage, wet gums are heated to 80° C. and thoroughly mixed with 10% wt propionic acid. Propionic acid addition to wet gums not only changed its viscosity and flowability but also reduced the pH to about 3, thereby partially hydrolyzing the phospholipids. The resulting wet gums mixture is dewatered by passing through a centrifuge. The water had lower salt content and lower organic content making it easy to handle/treat. In the second stage, the lipid phase is heated and sulfuric acid is added to complete the hydrolysis process. Due to the lower volume and lower pH of the material the amount of sulfuric acid required to complete the hydrolysis step is less. The final reaction mixture is allowed to settle in an oven at 80° C. High oil yield was observed with very little fallout. Moisture in the oil phase was lower (5.5%) than that from single stage process (14.4%). Therefore, two-stage process can be an alternative option other than traditional single stage hydrolysis process for better oil yield with lower moisture and AI content.

Chemical Hydrolysis of Dry Gums

Dry gums, unless the properties of the gums are being altered during the drying process, should essentially result in similar reaction yields upon chemical hydrolysis. Table 7 shows that addition of organic acids and/or glycerin as solvents to dry gums showed oil yields as similar to wet gums. Moreover, hydrochloric acid and sulfuric acid has similar effect during hydrolysis reaction.

TABLE 7

Chemical Hydrolysis of Dry Gums

|   |   |   | 8 hour settling | | Moisture |
| --- | --- | --- | --- | --- | --- |
| No | Treatment | End pH | Oil % | Emulsion % | in oil phase, % |
| 1 | Dry gums + SA | 1.52 | Little oil layer, lots of fallout | | |
| 2 | Dry gums + 10% PA + SA | 1.57 | 72 | 28 (fallout) | 2.66 |
| 3 | Dry gums + 10% PA + HCl | 1.67 | 66 | 34 (fallout) | 5.86 |
| 4 | Dry gums + 10% AA + HCl | 1.80 | 44 | 56 (fallout) | 2.75 |
| 5 | Dry gums + 20% GLY + SA | 1.49 | 52 | 48 (fallout) | |

Processing Wet Gums and Dry Gums Combination

Combination of 50% wet gum and a 50% dry gum was made and hydrolyzed using propionic acid as solvent. According to Table 8, the combination of wet gums and dry gums showed best result with addition of 10% propionic acid. Addition of 10% acetic acid gave the same result.

TABLE 8

Hydrolysis of Dry gums/Wet Gums combinations

|   |   | 8 hour settling | | | Moisture |
| --- | --- | --- | --- | --- | --- |
| Treatment | End pH | Oil % | Emulsion % | Water % | in oil phase, % |
| Wet gums + Dry gums + SA | 1.38 | 43 | 57 (fallout) | | 0.76 |
| Wet gums + Dry gums + 10% PA + SA | 1.55 | 66 | 3 | 32 | 10.22 |
| Wet gums + Dry gums + 10% AA + SA | 1.51 | 66 | 3 | 32 | 7.21 |

C. Option 3: Liquid Feed/Mold Inhibitor Product by Combining with Organic Acids

Wet gums, although nutritionally desirable, find limited application in feed due to their handling and storage difficulties. Organic acids, like propionic acid, besides being an excellent mold inhibitors overcomes these problems of gums. Development of such a product may offer a cost effective and more nutritious feed additive to improve shelf life of feed, high moisture grain/grain products from ethanol, and silage to name a few. In this study wet gums and propionic acid were mixed and judged for flowability and pourability. The propionic acid was neutralized to pH 5.2 using ammonium hydroxide. The following mixture was made:

73% Wet gums, 20% propionic acid, ~7% $NH_4OH$
Initial flowability of the wet gums alone was like pudding. Adding propionic acid lead to an increase in flowability, moving much like water.
After neutralization with $NH_4OH$, the flowability remained high, becoming only slightly less flowable.

Propionic acid plays a dual role in the wet gums. Firstly, it makes the wet gums more flowable and easily pumped. Secondly, it acts as a preservative. Propionic acid acts as an effective preservative at the 0.02% level. The ratio of propionic acid in the liquid blend must be high enough so that when added to feed it will be present at a 0.02% level.

Option 4: Dry Feed Product by Combining with Agricultural Co-Products

It was identified that new feed products can be developed by mixing wet gums with specific feed ingredients including soy meal, corn gluten meal, vegetable oil, soy hulls, dried distiller grains etc. The dry ingredients were previously ground into flour using a blender before they are mixed with wet gums. The calcium oxide (CaO) and o-phosphoric acid play dual roles as both drying agents and as sources of nutrition. It is important for the dry blend to have low moisture content because moisture content is most critical for preservation.

Given below are some formulations of new feed products:

65% soybean meal flour, 35% wet gums
The soybean meal flour and wet gums were mixed thoroughly and then dried in a 60° C. oven for eight hours. The initial moisture was 15.23% and the final moisture after heating was 5.48%. This product was balled up and oily. It was not free moving.

62% soybean meal flour, 3% CaO, 33% wet gums, 2% (85% o-phosphoric acid)
Firstly, the CaO was mixed with the soybean meal flour. Secondly, the phosphoric acid was added to the wet gums. After preparing both the soybean meal flour and wet gum mixtures independently, the mixtures were added together and mixed thoroughly. The mixture was then dried in a 60° C. oven for eight hours. The initial moisture was 15.75% and the final moisture after heating was 3.98%. This mixture appeared less oily compared to the first mixture without any drying agents. It was free moving with balled up pieces.

59% soybean meal flour, 4.5% CaO, 32% wet gums, 4.5% o-phosphoric acid.
Firstly, the CaO was mixed with the soybean meal flour. Secondly, the phosphoric acid was added to the wet gums. After preparing both the soybean meal flour and wet gum mixtures independently, the mixtures were added together and mixed thoroughly. The mixture was then dried in a 60° C. oven for eight hours. The initial moisture was 16.74% and the final moisture after heating was 3.31%. This mixture appeared less oily compared to the first mixture without any drying agents. In addition, it was free moving with scant balled up pieces.

60% soybean meal flour, 5% CaO, 30% wet gums, 5% phosphoric acid
Firstly, the CaO was mixed with the soybean meal flour. Secondly, the phosphoric acid was added to the wet gums. After preparing both the soybean meal flour and wet gum mixtures independently, the mixtures were added together and mixed thoroughly. Mixture warmed when two mixtures were combined. Final temperature was 36° C. Before drying the soybean meal flour and wet gums feel oily to the touch and can be easily molded into pieces that stay together. The mixture was then dried in a 60° C. oven for eight hours. The initial moisture was 16.13% and the final moisture after heating was 2.97%. The pH was 7.26. The final product was free flowing.

60% corn gluten meal, 5% CaO, 30% wet gums, 5% phosphoric acid
Firstly, the CaO was mixed with the corn gluten meal. Secondly, the phosphoric acid was added to the wet gums. After preparing both the corn gluten meal and wet gum mixtures independently, the mixtures were added together and mixed thoroughly. Mixture warmed when two mixtures were combined. Final temperature was 37° C. Before drying the corn gluten meal and wet gum mixture is very fine and movable, like sand that is slightly moist. The mixture cannot readily be molded into pieces. If pieces are formed they crumble easily. The mixture was then dried in a 60° C. oven for eight hours. The initial moisture was 16.10% and the final moisture after heating was 2.45%. The pH was 6.95. The final product was free flowing.

60% Distillers dried grains, 5% CaO, 30% wet gums, 5% phosphoric acid
Firstly, the CaO was mixed with the distillers dried grains (DDG) flour. Secondly, the phosphoric acid was added to the wet gums. After preparing both the DDG flour and wet gum mixtures independently, the mixtures were added together and mixed thoroughly. Initial temperature of the DDG mixture was 29° C. and the wet gums mixture was 24° C. When combined the temperature warmed to 38° C. Before drying the DDG mixture was clumpy and sticky and not freely moving. It balled easily into large clumps and did not break apart readily. The mixture was then dried in a 60° C. oven for eight hours. The initial moisture was 16.77% and the final moisture after heating was 3.09%. The pH was 6.78. The final product was free flowing.

CONCLUSIONS

Enzymes are able to hydrolyze soapstock/wet gums and produce clear oil, reduce the emulsion and release clear water. Other major outcome of this study is that the proteases were also able to hydrolyze soapstock at neutral pH. Phospholipase A2 worked effectively than others. Post centrifugation should be considered to obtain better oil yield and reduce emulsion.

The present invention shows that wet gum, dry gum with high phospholipid content, can be successfully hydrolyzed with high oil yields both by chemical and enzymatic processing. Enzymes can selectively hydrolyze the phospholipids to release free fatty acids. The addition of solvents such as propionic acid and glycerin considerably increased the oil yield. Mass balance studies showed similar results to small scale experiments. Some other options like drying process or blending with other agricultural co-products may also have good commercial value.

We claim:

1. A method of producing fatty-acid-rich oil from a by-product from vegetable oil refining, the by-product being selected from a group consisting of soapstocks and wet gums, the method comprising the steps of:
    mixing the by-product with a solvent prior to a hydrolysis step, said solvent comprising glycerin;
    adding caustic to the by-product to adjust the pH of the by-product to an optimal working pH range of an enzyme selected from a group consisting of phospholipase A1, phospholipase A2, phospholipase C, lipase, and protease;
    adding the enzyme to the by-product to hydrolyze the by-product into fatty-acid-rich oil containing free fatty acids and phosphatide molecules, and to split the by-product into a fatty-acid-rich oil phase, an emulsion phase and a water phase; and
    separating the fatty-acid-rich oil phase.

2. The method of claim 1, wherein the by-product is soapstock, and wherein the viscosity of the soapstocks is adjusted by adjusting the moisture content of the soapstocks to about 70% by weight.

3. The method of claim 2, wherein the soapstock is heated to about 55° C. and stirred before the pH of the by-product is adjusted.

4. The method of claim 2, wherein the enzyme is added to a concentration of about 2% by weight.

5. The method of claim 2, wherein the fatty-acid-rich oil is separated by settling and/or centrifuging.

6. The method of claim 1, wherein the by-product is wet gums, and wherein the viscosity of the wet gums is adjusted by mixing with acid oil.

7. The method of claim 6, wherein the wet gum is heated to about 50° C. and stirred before the pH of the by-product is adjusted.

8. The method of claim 6, wherein the enzyme is added to a concentration of about 0.5 to 2.0%.

9. The method of claim 8, wherein the enzyme is phospholipase A2.

10. The method of claim 6, wherein the fatty-acid-rich oil is separated by settling and/or centrifuging.

11. The method of claim 1, wherein the by-product is wet gum dried to a dry gum to prevent spoilage.

12. The method of claim 11, wherein the dry gum is heated to about 45° C. to 60° C.

13. The method of claim 11, wherein the enzyme is added to a concentration of about 0.5 to 2% by weight.

* * * * *